United States Patent [19]

Guthrie et al.

[11] 4,061,864

[45] Dec. 6, 1977

[54] THIOL CONTAINING COMPOUNDS AND THEIR PREPARATION

[75] Inventors: James Leverette Guthrie, Ashton; Shrikant Vishwanath Dighe, Bethesda, both of Md.

[73] Assignee: W. R. Grace & Co., New York, N.Y.

[21] Appl. No.: 652,239

[22] Filed: Jan. 26, 1976

Related U.S. Application Data

[63] Continuation-in-part of Ser. No. 408,338, Oct. 23, 1973, abandoned, which is a continuation-in-part of Ser. No. 393,862, Sept. 4, 1973, Pat. No. 3,883,598.

[51] Int. Cl.$^2$ .......................................... C07C 101/447
[52] U.S. Cl. .................................... 560/26; 560/115; 560/158
[58] Field of Search ........... 260/471 C, 455 A, 468 E, 260/482 B

[56] References Cited

U.S. PATENT DOCUMENTS 3,142,699   7/1964   Wagner et al. ...................... 260/471

*Primary Examiner*—R. Gallagher
*Assistant Examiner*—Lisa Jones
*Attorney, Agent, or Firm*—Richard P. Plunkett; William W. McDowell, Jr.

[57] ABSTRACT

This invention is directed to thiol containing compounds having no hydrolytically sensitive groupings which are useful as polymerization transfer agents or as curing agents in curable polymer systems containing polyenes and a free radical initiator. The thiol containing compounds are formed by reacting a polyol with an allylic halide to form a poly(unsaturated ether) whose double bonds are converted to thioesters by free radical catalyzed addition of SH groups from a thiolcarboxylic acid, e.g. thioacetic acid and the like. Hydrolysis of the thioester yields the desired thiol or polythiol derivative. Alternatively the poly(unsaturated ether) is reacted with $H_2S$ to give the desired thiol or polythiol directly in a single step. The polythiols can be chain extended by any difunctional compound that reacts with the hydroxy groups on the polythiol.

2 Claims, No Drawings

THIOL CONTAINING COMPOUNDS AND THEIR PREPARATION

This application is a continuation-in-part of copending application having Ser. No. 408,338, filed Oct. 23, 1973, now abandoned which in turn is a continuation-in-part of application having Ser. No. 393,862, filed Sept. 4, 1973, now U.S. Pat. No. 3,883,598.

This invention relates to thiol containing compounds and their preparation. More particularly this invention is directed to thiol containing compounds having no hydrolytically sensitive groupings.

Commercially available polythiols are usually esters of 3-mercaptopropionic or 2-mercaptoacetic acid with polyols such as trimethylol propane or glycerol. However, these ester-containing compounds hydrolyze quite readily in the presence of water or humid environments in both the cured and uncured state.

One object of the instant invention is to produce a mono or polythiol which is hydrolytically stable. Other objects can be ascertained from a reading hereinafter.

In the present invention, the thiol containing compounds are formed by reacting in the presence of a base, a polyol of the general formula: $HO-R-(OH)_m$ wherein R is the backbone of a saturated aliphatic polyol consisting of atoms of carbon, hydrogen and oxygen and free of reactive functional groups, said polyol containing up to 60 carbon atoms and m is an integer of 1 to 7 with an allylic halide of the general formula:

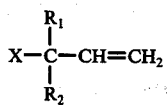

wherein $R_1$ and $R_2$ are independently selected from the group consisting of hydrogen, methyl and ethyl radical and X is chloride, bromide or iodide to form a poly(unsaturated) ether of the formula:

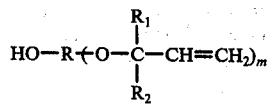

The poly(unsaturated) ether is converted to thioester by free radical catalyzed addition of SH groups from well known, commercially available thiolcarboxylic acid such as thiopropionic acid, thioacetic acid, thiobenzoic acid and the like. Hydrolysis of the thioester in the presence of acid or base yields the desired thiol or polythiol derivative or alternatively the poly(unsaturated) ether) is reacted with $H_2S$ directly in a single step to give the desired thiol or polythiol of the formula:

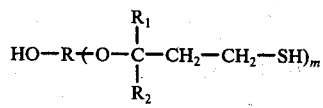

The thus formed polythiols of the instant invention can thereafter, if desired, be coupled by various means. That is, any difunctional compound that reacts with the hydroxy group on the polythiol is operable to chain extend the polythiol. Thus for example any di or poly isocyanate, carbodiimide or dianhydride can be used herein to couple the polythiols formed by the instant invention. For example an ether thiol of the formula:

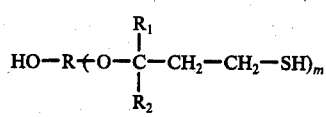

wherein $R_1$ and $R_2$ are independently selected from the group consisting of hydrogen, methyl and ethyl; R is the backbone of a saturated aliphatic polyol consisting of atoms of carbon, hydrogen and oxygen and free of reactive functional groups, said polyol containing up to 60 carbon atoms and m is an integer of 1 to 7 is admixed with an isocyanate of the formula:

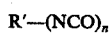

$$R'-(NCO)_n$$

wherein R' is a polyvalent organic moiety and n is at least 2, said ether thiol being present in an amount sufficient to react stoichiometrically with the NCO groups in the isocyanate to form a chain extended ether thiol of the formula:

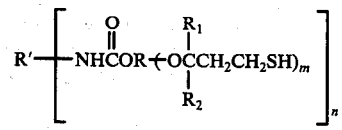

wherein $R_1$ and $R_2$ are independently selected from the group consisting of hydrogen, methyl and ethyl; R is the backbone of a saturated aliphatic polyol consisting of atoms of carbon, hydrogen and oxygen and free of reactive functional groups, said polyol containing up to 60 cabon atoms, R' is a polyvalent organic moiety, m is an integer of 1 to 7 and n is at least 2. The reaction is carried out under ambient conditions, i.e. room temperature and atmospheric pressure for a period ranging from 12–24 hours. Conventional catalysts such as tertiary amines, ferric chloride and stannous octoate can be employed if desired in catalytic amounts to speed up the reaction.

Following the reaction of the NCO groups in the polyisocyanate with the hydroxy group in the ether thiol, the R' in the polyisocyanate remaining is a polyvalent organic moiety consisting of the residue of the polyisocyanate. Although all polyisocyanates containing at least two NCO groups are operable herein, the choice of one is usually made on the basis of commercial availability. Polyisocyanates which are commercially available include, but are not limited to PAPPI-1 (a polyaryl polyisocyanate as defined in U.S. Pat. No. 2,683,730), tolylene diisocyanate, triphenylmethane-4,4'4",-triisocyanate, benzene-1,3,5-triisocyanate, toluene-2,4,6-triisocyanate, diphenyl-2,4,4'-triisocyanate, hexamethylene diisocyanate, xylene diisocyanate, chlorophenylene diisocyanate, diphenylmethane-4,4'-diisocyanate, naphthalene-1, 5-diisocyanate, 3,3'-dimethyl-4,4'-biphenylene diisocyanate, 2,2',5,5'-tetramethyl-4,4'-biphenylene diisocyanate, 4,4'-methylenebis (phenylisocyanate), 4,4'-sulfonylbis (phenylisocyanate), 4,4-methylene di-orthotolylisocyanate, ethylene diisocyanate, trimethylenediisocyanate, 4,4'-diphenylmethane diisocyanate, isophorone diisocyanate, dianisidine diisocyanate, o-tolidine diisocyanate, m-tolidine diisocyanate, hexmethylene diisocyanate, 2,2,4-trimethyl-hexamethylene diisocyanate, 2,4,4-trimethyl-hexamethylene diisocyanate, 4,4'-dicyclohexylmethane diisocyanate, diphenylether 4-4'-diisocyanate, 1,3-bis(isocyanomethyl)cyclobutane, polymethylene polyphenyl isocyanate, naphthalene diisocyanate, tolylene diisocyanate, m-xylylene diisocyanate, p-xylylene diisocyanate, 3,3'-bitolylene-4,4'-diisocyanate and the like.

The reaction for forming the poly(unsaturated) ether is usually carried out at a temperature ranging from about 40° to 95° C at atmospheric pressure. At superatmospheric pressure (up to 200 psi) higher temperatures can be employed. The reaction time is usually 6–14 hours. The allyl halide is added in an excess ranging from 100% to 400% of the stoichiometric amount necessary to react with all but one of the hydroxyl groups on the polyol.

The amount of base, e.g. NaOH, added ranges from a stoichiometric amount required to react with the liberated halogen acid up to 50% excess. Even greater amounts are operable but unnecessary.

The amount of thiolcarboxylic acid added is an amount sufficient to react stoichiometrically with the unsaturated carbon to carbon bonds in the poly(unsaturated) ether. An excess over the stoichiometric amount can be added but is not necessary. Operable thiolcarboxylic acids include but are not limited to thioacetic acid, thiopropionic acid, thiobenzoic acid and the like.

The reaction can be dried with any well known drying agent such as calcium sulphate, anhydrous magnesium sulphate, potassium carbonate and the like.

In carrying out the reaction, if desired, a catalyst can be used. Such catalysts include iodide salts such as sodium iodide, potassium iodide and the like. The catalyst is added in an amount ranging from about 1 to 2% by weight of the polyol.

In the polyol of the general formula: HO—R—(OH)$_m$ supra, following the reaction with the allylic halide, R is the backbone of a saturated aliphatic polyol consisting of atoms of carbon, hydrogen and oxygen, containing up to 60 carbon atoms and free of reactive functional groups. Although any polyol within the above definition is operable herein, the choice is usually made on the basis of commercial availability. Polyols which are commercially available for use herein include, but are not limited to, ethylene glycol, propylene glycol, 1,4-butanediol, pentaerythritol, dipentaerythritol, tripentaerythritol, trimethylolpropane, trimethylolethane, glycerol, diglycerol, erythritol, sorbitol, inositol, diethylene glycol, dipropylene glycol, mannitol and the like. Additionally, poly(oxyethylene or oxypropylene) glycols with molecular weights up to about 2,500 can be used per se or to chain-extend the aforelisted polyols.

The following examples are set out to explain but expressly not limit the instant invention. Unless otherwise stated, all parts and percentages are by weight.

EXAMPLE I

Triallyl Ether of Pentaerythritol

Into a 5 liter three-necked flask fitted with condenser and addition funnel was placed a solution of 650 g. (16.25 equivalents) of sodium hydroxide in 650 ml. of water. To this was added 272 g. (two moles) of pentaerythritol. This mixture was stirred by means of a magnetic bar and heated to 70° C. Then 1936 g. (1385 ml., 16 moles) of allyl bromide was added over an 8-hour period at such a rate that the temperature stayed between 70° and 80° C. Following this, heating was resumed, keeping the temperature at 80°-82° C for an additional 4 hours. Volatile materials were removed by distillation at atmospheric pressure until the temperature of the condensing vapor reached 98° C.

One liter of water was added to the hot residue (to prevent crystallization of the salts). The product was cooled to room temperature and the layers were separated. The water layer was extracted twice with 300 ml. portions of diethyl ether. The combined organic layers were dried over anhydrous magnesium sulfate and then distilled at atmospheric pressure to remove the diethyl ether. The triallyl ether of pentaerythritol product, i.e.

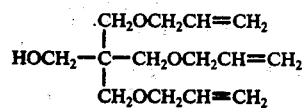

weighed 451 g. (88% conversion). The infrared and NMR spectra were those expected for the triallyl ether of pentaerythritol. The triallyl ether of pentaerythritol product had a boiling range of 120°-121° C. at 1 mm., $n_{D24}$ 1.4625.

EXAMPLE II

Example I was repeated except that 1088 g. (9 moles) of allyl bromide instead of 1936 (16 moles) were used. The resulting product was the same.

EXAMPLE III

Into a 5 liter, stainless steel, closed reactor was placed a solution of 650 g. of sodium hydroxide in 650 ml. of water. To this was added 272 grams (2 moles) of pentaerythritol. The mixture was stirred and heated to 70° C. 918 g. (12 moles) of allyl chloride was added under pressure over a 6 hour period at such a rate that the temperature was maintained between 90°-95° C for an additional 4 hours. The reactor was cooled and the product was removed from the reactor and charged to distillation apparatus wherein the volatile materials were removed by distillation at atmospheric pressure until the temperature of the condensing vapor reached 98° C.

One liter of water was added to the hot residue (to prevent crystallization of the salts). The product was cooled to room temperature and the layers were separated. The water layer was extracted twice with 300-ml. portions of diethyl ether. The combined organic layers were dried over anhydrous magnesium sulafte and then distilled at atmospheric pressure to remove the diethyl ether. The triallyl ether of pentaerythritol product weighed 436 g. 85% conversion). The infrared and NMR spectra were those expected for the triallyl ether. The triallyl ether of pentaerythritol product had a boiling range of 120°-121° C. at 1 mm.; $n_D{}^{24}$ 1.4625.

EXAMPLE IV

Conversion of Triallyl Ether to Trithiol

Ten drops of tert-butyl hydroperoxide was added to 85.2 g (1 equivalent of unsaturation) of pentaerythritol triallyl ether from Example I in a 500-ml. flask equipped with a condenser and magnetic stirrer. This mixture was heated to 40° C., and 76 g. (1 mole) of thiolacetic acid was added during one hour at such a rate that the temperature did not exceed 90° C. After the addition was complete, the product was kept at 80° C. for an hour and then allowed to cool to room temperature overnight.

To the product was added a solution of 100 g. (2.5 eq) of sodium hydroxide in 200 ml. of water. This mixture was heated under reflux for 3 hours and then cooled to room temperature and diluted with 300 ml. of ether to facilitate separation of the layers. After separation, the water layer was acidified to pH 2-5 with HCl and then extracted twice with 400-ml. portions of ether. Ether was evaporated from the combined organic layers, and the residue was diluted with an equal volume of toluene. The resulting solution was washed with 5% aqueous sodium bicarbonate, then with 5% aqueous hydrochloric acid, and with water. The toluene and other volatile contaminants were removed by distillation at 0.1 mm. Hg until the temperature of the residue reached 225° C. The product (pentaerythritol tris (γ-mercaptopropyl) ether, i.e.

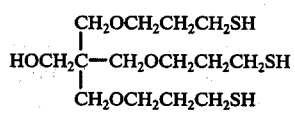

weighed 119 g. (100% conversion) and had a mercaptan content of 7.09 meq/g. This is 84.6% of the theoretical amount.

Part of the trithiol was distilled at 0.1 mm. Hg. The distillate had a boiling range of 243°-245° C and a mercaptan content of 7.88 meq/g (94% of theoretical value).

EXAMPLE V

Conversion of Triallyl Ether to Trithiol 85.2 g. (1 equivalent of unsaturation) of pentaerythritol triallyl ether was placed in a 500-ml. flask equipped with a condenser and magnetic stirrer. This mixture was heated to 40° C., and 76 g. (1 mole) of thiolacetic acid was added at once. After the addition was complete, the product was irradiated for 24 hours with a high intensity UV mercury vapor lamp at a surface intensity of 8000 microwatts/cm² and then allowed to cool to room temperature overnight.

To the product was added a solution of 100 g. (2.5 eq) of sodium hydroxide in 200 ml. of water. This mixture was heated under reflux for three hours and then cooled to room temperature and diluted with 300 ml. of ether to facilitate separation of the layers. After separation, the water layer was acidified to pH 2-5 with HCl and then extracted twice with 400-ml. portions of ether. Ether was evaporated from the combined organic layers, and the residue was diluted with an equal volume of toluene. The resulting solution was washed with 5% aqueous sodium bicarbonate, then with 5% aqueous hydrochloric acid, and with water. The toluene and other volatile contaminants were removed by distillation at 0.1 mm. HG until the temperature of the residue reached 225° C. The product weighed 119 g. (100% conversion) and had a mercaptan content of 7.2 meq/g.

EXAMPLE VI 25.6 g. (0.1 mole) of pentaerythritol triallyl ether from Example I was dissolved in 68 g. (2 moles) of hydrogen sulfide at −70° C and irradiated for 3 hours at a surface intensity of 8000 microwatts/cm² from a high intensity mercury vapor lamp whose effective wavelength is 254 microns. The mixture was then warmed to room temperature allowing the unreacted hydrogen sulfide to evaporate. The resulting solution was washed with 5% aqueous sodium bicarbonate, then with 5% aqueous hydrochloric acid and then with water. The pentaerythritol tris (γ-mercaptopropyl) ether product weighed 36.0 grams and has a mercaptan content of 7.1 meq/g.

EXAMPLE VII

Allyl Ether of Diethylene Glycol

Into a 1 liter, three-necked flask fitted with condenser and addition funnel was placed a solution of 44 g. (1.1 equivalents) of sodium hydroxide in 44 ml. of water. To this was added 106 g. (one mole) of diethylene glycol. This mixture was stirred by means of a magnetic bar and heated to 70° C. Then, 229.5 g. (3 moles) of allyl chloride was added over an 8-hour period at such a rate that the temperature stayed between 70° and 80° C. Following this, heating was resumed, keeping the temperature at 80°-82° C. for an additional 4 hours. Volatile materials were removed by distillation at atmospheric pressure until the temperature of the condensing vapor reached 98° C.

100 ml. of water was added to the hot residue (to prevent crystallization of the salts). The residue was cooled to room temperature and the layers were separated. The water layer was extracted twice with 50 ml. portions of diethyl ether. The combined organic layers were dried over anhydrous magnesium sulfate and then distilled at atmospheric pressure to remove the diethyl ether. The residue weighed 162 g. (90% conversion). The infrared and NMR spectra were those expected for the mono allyl ether of diethylene glycol.

The following examples show the use of the polythiols of this invention to crosslink polyenes and also show the use of the monothiols of the instant invention as chain transfer agents.

EXAMPLE VIII

A polyene was prepared in the following manner.

A round bottom flask is fitted with a stirrer, thermometer, dropping funnel, nitrogen inlet and outlet. The flask can be placed in a heating mantle or immersed in a water bath as required.

Two moles (428 gms.) of trimethylol-propane diallyl ether were mixed with 0.2 cc. of dibutyl tin dilaurate under nitrogen. One mole of tolylene-2,4-diisocyanate was added to the mixture, using the rate of addition and cooling water to keep the temperature under 70° C. The mantle was used to keep the temperature at 70° C for another hour. Isocyanate analysis showed the reaction to be essentially complete at this time resulting in the following viscous product:

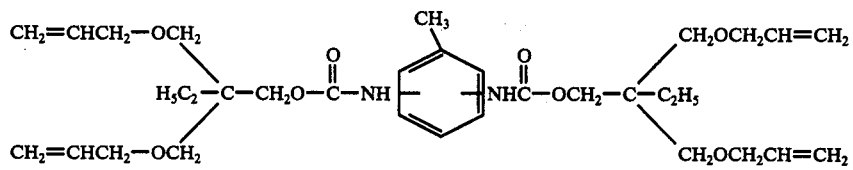

which will be referred to hereinafter as Prepolymer A.

15.0 g. (0.1 equivalent or unsaturation) of Prepolymer A was admixed with 11.9 g. (0.1 equivalent of thiol) of the polythiol from Example IV along with 0.3 g. of benzophenone (a photocuring rate accelerator). A 40 mil thick film of the admixture was placed under a 275 watt sunlamp delivering 4000 microwatts/cm$^2$ at the film surface at a distance of 10 inches and irradiated with UV light for 5 minutes. The resulting cured elastomeric film had a tensile strength of 588 psi, elongation at failure of 54% and a tensile modulus at 1% elongation of 3220 psi.

EXAMPLE IX

An improved polythiol crosslinking agent was prepared by mixing 71.6 g. (0.2 mole) of the polythiol from Example IV with 17.4 g. (0.1 mole) of toluene diisocyanate and thereafter allowing the mixture to stand for 1 day at room temperature, 25° C. The resulting viscous hexathiol was used to make a cured polymer film as in the previous example using 15.0 g. (0.1 equivalent) of Prepolymer A and 14.8 g. (0.1 equivalent thiol) of hexathiol. After irradiation as in the previous example, the resulting glassy film had a tensile strength of 5900 psi, an elongation at failure of 6% and a tensile modulus at 1% elongation of 152,000 psi.

EXAMPLE X

To the monoallyl ether of diethylene glycol product from Example VII was added 76 g. (1 mole) of thiolacetic acid over a 1 hour period at such a rate that the temperature did not exceed 90° C. After the addition was complete, the product was kept at 80° C. for an hour and then allowed to cool to room temperature overnight.

To the product was added a solution of 100 g. (2.5 eq) of sodium hydroxide in 200 ml. of water. This mixture was heated under reflux for three hours and then cooled to room temperature and diluted with 300 ml. of ether to facilitate separation of the layers. After separation, the water layer was acidified to pH 2–5 with HCl and then extracted twice with 400-ml. portions of ether. Ether was evaporated from the combined organic layers, and the residue was diluted with an equal volume of toluene. The resulting solution was washed with 5% aqueous sodium bicarbonate, then with 5% aqueous hydrochloric acid, and with water. The toluene and other volatile contaminants were removed by distillation at 0.1 mm. Hg until the temperature of the residue reached 225° C. The product, i.e. mono γ-thiopropyl ether of diethylene glycol was obtained in good yield.

This example shows the use of the monothiol as a chain transfer agent.

EXAMPLE XI 50 g. of acrylonitrile, 50 g. of methyl acrylate, 200 ml. of water, 0.06 g. of potassium persulphate and 3.0 g. of sodium lauryl sulphate (emulsifier) were charged to a 1 liter reactor equipped with stirrer and condenser. The reactor was heated to 60° C and stirred at 300 RPM for 6 hours. The resulting copolymerized product from the emulsion polymerization was coagulated by adding 5 g. of aluminum sulphate in 100 ml. water and agitating at 500 RPM for ½ hour. The thus coagulated copolymer was separated by centrifugation and water washed until the wash water was clear. The copolymer was dried at 70° C. The melt index of the copolymer product was measured under a standard load of 2160 g. at 190° C in accord with the conditions specified in ASTM D-1238-52T. The copolymer had a melt index of 0.0.

The above example was repeated except that 1.0 g. of the mono γ-thiopropyl ether of diethylene glycol from Example X was charged to the reactor along with the other ingredients. The resulting copolymer product had a melt index of 5.8 indicating a lower molecular weight copolymer due to the presence of the monothiol as a chain transfer agent.

The following example shows the hydrolytic stability of the polythiols of the instant invention over conventional commercially available ester-type polythiols.

EXAMPLE XII

The polythiol from Examples IV and IX herein were admixed in stoichiometric amounts with either Prepolymer A from Example VIII or triallyl isocyanurate, a commercially available polyene manufactured by Allied Chemical Company. The same polyenes were admixed stoichiometrically with pentaerythritol tetrakis (β-mercaptopropionate), a commercially available ester-type polythiol. To each admixture was added 1% by weight of the polyene and polythiol of benzophenone as a photocuring rate accelerator. The admixtures were spread out in a film of 20 mil thickness and irradiated with a 275 watt UV sunlamp delivering 4000 microwatts/cm$^2$ at the film surface for a period of 5 minutes. The tensile strength and 1% modulus were measured on each film sample. The cured, solid films were then placed in boiling water. After the stated times in boiling water, the tensile strength and 1% modulus were remeasured. The percent of the property retained is shown in Table I.

TABLE I

| Polyene | Polythiol | Hours Boiled | Percent of Property Retained | |
|---|---|---|---|---|
| | | | Tensile Strength | 1% Modulus |
| Triallyl Isocyanurate | Trithiol from Example IV | 66 | 100 | 113 |
| Triallyl Isocyanurate | Pentaerythritol tetrakis (β-mercaptopropionate | 66 | 15 | 1.4 |
| Prepolymer A from Example VIII | Trithiol from Example IV | 24 | 78 | 55 |
| Prepolymer A from Example VIII | Hexathiol from Example IX | 24 | 86 | 95 |
| Prepolymer A from Example VIII | Pentaerythritol tetrakis (β-mercaptopropionate | 24 | 28 | 19 |

Since hydrolysis of the film is indicated by a decrease in tensile strength and modulus, the data indicates that the film made from the ether polythiols of the instant invention are 3 to 4 times as stable hydrolytically as those made with commerically available ester-type polythiols.

EXAMPLE XIII

Diallyl Ether of Glycerol

Into a 5 liter three-necked flask fitted with condenser and addition funnel was placed a solution of 650 g. (16.25 equivalents) of sodium hydroxide in 650 ml. of water. to this was added 184 g. (two moles) of glycerol. This mixture was stirred by means of a magnetic bar and heated to 70° C. Then 1936 g. (1385 ml., 16 moles) of allyl bromide was added over an 8 hour period at such a rate that the temperature stayed between 70° and 80° C. Following this, heating was resumed, keeping the temperature at 80°-82° C. for an additional 4 hours. Volatile materials were removed by distillation at atmospheric pressure until the temperature of the condensing vapor reached 98° C.

One liter of water was added to the hot residue (to prevent crystallization of the salts). The product was cooled to room temperature and the layers were separated. The water layer was extracted twice with 300 ml. portions of diethyl ether. The combined organic layers were dried over anhydrous magnesium sulfate and then distilled at atmospheric pressure to remove the diethyl ether. The diallyl ether of glycerol product, i.e.

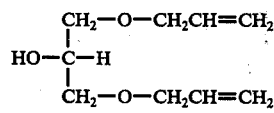

weighed 206 g. (60% conversion). The infrared and NMR spectra were those expected for the diallyl ether of glycerol. The diallyl ether of glycerol product had a boiling range of 104°-106° C. at 6 mm.

EXAMPLE XIV

Conversion of Diallyl Ether to Dithiol

Ten drops of tert-butyl hydroperoxide was added to 86.0 g. (1 equivalent of unsaturation) of glycerol diallyl ether from Example XIII in a 500-ml. flask equipped with a condenser and magnetic stirrer. This mixture was heated to 40° C., and 76 g. (1 mole) of thiolacetic acid was added during one hour at such a rate that the temperature did not exceed 90° C. After the addition was complete, the product was kept at 80° C. for an hour and then allowed to cool to room temperature overnight.

To the product was added a solution of 100 g. (2.5 eq) of sodium hydroxide in (200 ml. of water. This mixture was heated under reflux for three hours and then cooled to room temperature and diluted with 300 ml. of ether to facilitate separation of the layers. After separation, the water layer was acidified to pH 2-5 with HCl and then extracted twice with 400-ml. portions of ether. Ether was evaporated from the combined organic layers, and the residue was diluted with an equal volume of toluene. The resulting solution was washed with 5% aqueous sodium bicarbonate, then with 5% aqueous hydrochloric acid, and with water. The toluene and other volatile contaminants were removed by distillation at 0.1 mm. Hg until the temperature of the residue reached 225° C. The product glycerol bis (γ-mercaptopropyl) ether, i.e.

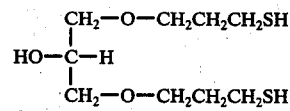

weighed 120 g. (100% conversion) and had a mercaptan content of 7.1 meq/g. This is 85% of the theoretical amount.

EXAMPLE XV

A polythiol crosslinking agent was prepared by mixing 48.0 g. (0.2 mole) of the polythiol from Example XIV with 17.4 g. (0.1 mole) of toluene diisocyanate and thereafter allowing the mixture to stand for 1 day at room temperature, 22° C. The resulting viscous tetrathiol was used to make a cured solid polymer film as in Example IX using 15.0 g. (0.1 equivalent) of Prepolymer A and 16.3 g. (0.1 equivalent thiol) of tetrathiol.

EXAMPLE XVI

Triallyl Ether of a Poly(oxypropylene) Tetrol

Into a 5 liter three-necked flask fitted with condenser and addition funnel was placed a solution of 650 g. (16.25 equivalents) of sodium hydroxide in 650 ml. of water. To this was added 680 g. (one mole) of a commercially available tetrol made by chain-extending pentaerythritol with propylene oxide. This mixture was stirred by means of a magnetic bar and heated to 70° C. Then 968 g. (692 ml., 8 moles) of allyl bromide was added over an eight-hour period at such a rate that the temperature stayed between 70 and 80° C. Following this, heating was resumed, keeping the temperature at 80°-82° C. for an additional four hours. Volatile materials were removed by distillation at atmospheric pressure until the temperture of the condensing vapor reached 98° C.

One liter of water was added to the hot residue (to prevent crystallization of the salts). The product was cooled to room temperature and the layers were separated. The water layer was extracted twice with 300 ml. portions of diethyl ether. The combined organic layers were dried over anhydrous magnesium sulfate and then distilled at atmospheric pressure to remove the diethyl ether. The triallyl ether product, i.e.

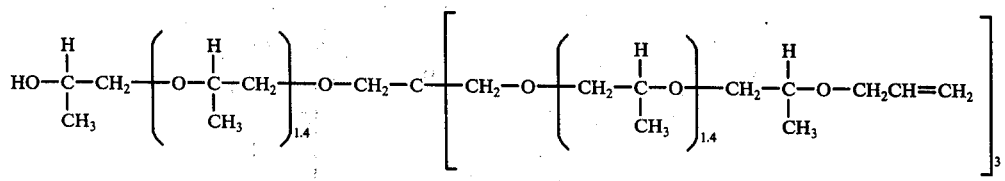

weighed 720 g. (85% conversion).

EXAMPLE XVII

Conversion of Triallyl Ether to Trithiol

Ten drops of tert-butyl hydroperoxide was added to 283 g. (1 equivalent of unsaturation) of the triallyl ether from Example XVI in a 1,000-ml. flask equipped with a condenser and magnetic stirrer. This mixture was heated to 40° C., and 76 g. (1 mole) of thiolacetic acid was added one hour at such a rate that the temperature did not exceed 90° C. After the addition was complete, the product was kept at 80° C. for an hour and then allowed to cool to room temperature overnight.

To the product was added a solution of 100 g. (2.5 eq) of sodium hydroxide in 200 ml. of water. This mixture was heated under reflux for three hours and then cooled to room temperature and diluted with 300 ml. of ether to facilitate separation of the layers. After separation, the water layer was acidified to pH 2-5 with HCl and then extracted twice with 400-ml. portions of ether. Ether was evaporated from the combined organic layers, and the residue was diluted with an equal volume of toluene. The resulting solution was washed with 5% aqueous sodium bicarbonate, then with 5% aqueous hydrochloric acid, and with water. The toluene and other volatile contaminants were removed by distillation at 0.1 mm. Hg until the temperature of the residue reached 225° C. The product, i.e.

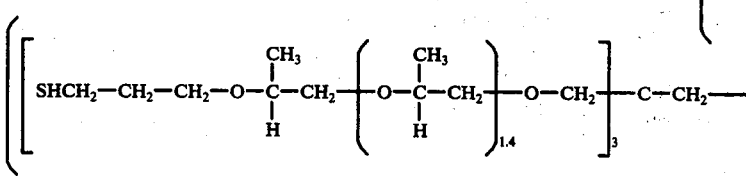

weighed 317 g. (100% conversion) and had a mercaptan content of 2.2 meq/g. This is 82% of the theoretical amount.

EXAMPLE XVIII

A polythiol crosslinking agent was prepared by mixing 190 g. (0.2 mole) of the polythiol from Example XVII with 17.4 g. (0.1 mole) of toluene diisocyanate and thereafter allowing the mixture to stand for 1 day at room temperature, 22° C. The resulting viscous hexathiol, i.e. of the formula:

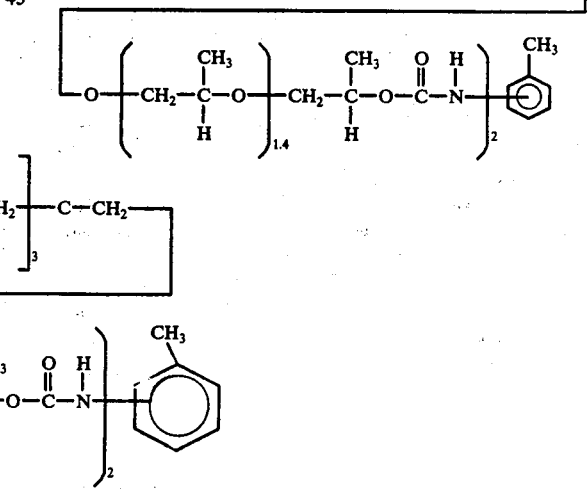

was used to make a cured solid polymer film as in Example IX using 15.0 g. (0.1 equivalent) of Prepolymer A and 17.9 g. (0.1 equivalent thiol) of hexathiol.

We claim:

1. An ether thiol of the formula:

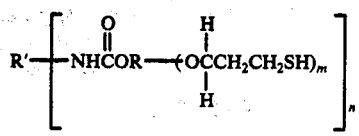

wherein R' is the polyvalent organic moiety consisting of the residue of a commercially available polyisocyanate after reaction of the NCO groups, R is the backbone of a saturated aliphatic polyol consisting of atoms of carbon, hydrogen and oxygen and free to reactive functional groups, said polyol containing up to 60 carbon atoms, m is an integer of 1 to 7 and n is at least 2.

2. An ether thiol selected from the group consisting of:

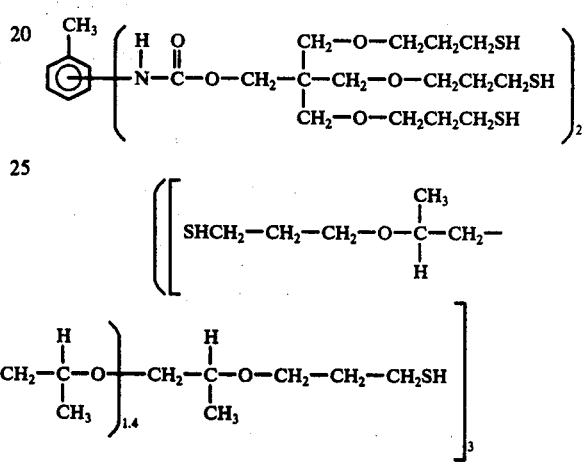

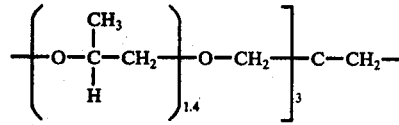

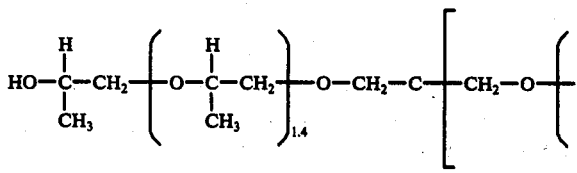

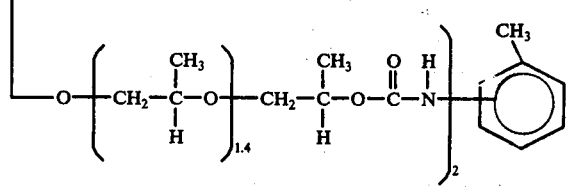

-continued
and
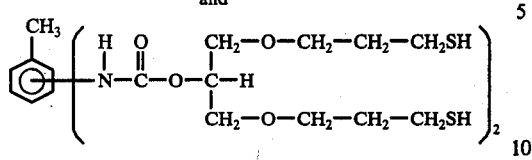
* * * * *

UNITED STATES PATENT AND TRADEMARK OFFICE
CERTIFICATE OF CORRECTION

PATENT NO. : 4,061,864
DATED : December 6, 1977
INVENTOR(S) : James L. Guthrie and Shrikant V. Dighe It is certified that error appears in the above-identified patent and that said Letters Patent are hereby corrected as shown below:

In Claim 1, column 12, line 13, delete the word "to" and insert therefor the word --of--.

Signed and Sealed this

Thirtieth Day of May 1978

[SEAL]

Attest:

RUTH C. MASON
Attesting Officer

LUTRELLE F. PARKER
Acting Commissioner of Patents and Trademarks